United States Patent [19]
Farone et al.

[11] Patent Number: 6,054,611
[45] Date of Patent: Apr. 25, 2000

[54] METHOD FOR THE PRODUCTION OF LEVULINIC ACID AND ITS DERIVATIVES

[75] Inventors: William A. Farone, Irvine; John E. Cuzens, Santa Ana, both of Calif.

[73] Assignee: Arkenol, Inc., Mission Viejo, Calif.

[21] Appl. No.: 09/076,941

[22] Filed: May 13, 1998

Related U.S. Application Data

[63] Continuation-in-part of application No. 08/747,441, Nov. 8, 1996, Pat. No. 5,892,107.

[51] Int. Cl.$^7$ .................................................. C07D 51/00
[52] U.S. Cl. ......................... 562/515; 549/429; 549/488; 549/489; 560/174
[58] Field of Search ............................................ 562/515

[56] References Cited

U.S. PATENT DOCUMENTS

| | | | |
|---|---|---|---|
| 2,206,311 | 7/1940 | Thompson | 562/515 |
| 2,270,328 | 1/1942 | Moyer | 562/515 |
| 2,305,738 | 12/1942 | Scheuing et al. | 562/515 |
| 2,813,900 | 11/1957 | Dunlop et al. | 562/515 |
| 2,840,605 | 6/1958 | Leonard | 562/515 |
| 3,701,789 | 10/1972 | Ramos-Rodriguez | 562/515 |
| 4,236,021 | 11/1980 | Hsu et al. | 560/174 |
| 4,897,497 | 1/1990 | Fitzpatrick | 549/489 |
| 5,562,777 | 10/1996 | Farone et al. | 127/37 |

FOREIGN PATENT DOCUMENTS

| | | |
|---|---|---|
| 1192293 | 10/1959 | France . |
| 2556344 | 6/1985 | France . |
| 705578 | of 0000 | Germany . |
| 619795 | 4/1961 | Italy . |
| 583533 | 12/1946 | United Kingdom . |
| WO 9423071 | 10/1994 | WIPO . |

OTHER PUBLICATIONS

The hydrogenation of 2–furaldehyde and its derivatives. G. Natta, R. Rigamonti and E. Beati, 23, 117–23 (1941), Chemical Abstracts, vol. 35, p. 5488–5489.
Levulinic acid. Wendell W. Moyer (to A.E. Staley Mfg. Co.). U.S. 2,270,328, Jan. 20, 10–Organic Chemistry, p. 3190.
Levulinic acid. Georg Scheuing and Wilhelm Konz (vested in the Alien Property Custodian). U.S. 2,305,738, Dec. 22, Chemical Abstracts, vol. 37, p. 3252.
Levulinic acid. Walter N. Haworth and Leslie F. Wiggins. Brit. 583,533, Dec. 20, 1946, Chemical Abstracts, 1947, p. 3123.
Derivatives of valerolactone, 1, 4–pentanediol, and 1, 4–bis (2–cyanoethoxy) pentane. Robert V. Christian, J. Am. Chem. Soc. 69, 1961–3 (1947), 10–Organic Chemistry, p. 6873–6874.
Levulinic acid. Holzhydrolyse Akt.–Ges. Ger. 700,643, Nov. 28, 1940, 10–Organic Chemistry, p. 6981.
Levulinic acid. Holzhydrolyse Akt.–Ges. Ger. 705,578, Mar. 27, 1941, Chemical Abstracts, vol. 36, p. 2079.
Levulinic acid. Alva Thompson (to Corn Products Refining Co.). U.S. 2,206,311, Jul., 2., Chemical Abstracts, vol. 34, p. 7299.
Organic Chemistry by Paul Karrer, Second English Edition, 1946, Elsevier Publishing Company, Inc., New York, Furan p. 737.
Furfural as a new decompotition product of glucose solution under oxygen atmosphere, Letters to the Editor, J. Pharm. Pharmac., 1978, 30, p. 668.
Practical Organic Chemistry including Qualitative Organic Analysis by Arthur I. Vogel, Third Edition, 1962, John Wiley & Sons, Inc., New York, N.Y., pp. 461–463.
Reagents for Organic Synthesis, Louis F. Fieser, 1967, John Wiley and Sons, Inc., New York, N.Y., pp. 564–566.
The Journal of the American Chemical Society, vol. LII, Sep.–Dec., 1930 by Arthur B. Lamb, "Levulinic Acid and its Esters" by Peter P.T. Sah and Shao–Yuan Ma, Dec. 18, 1930, vol. 52, pp. 4880–4883.
Levulinic acid recovery. Alexander D. Macallum (to E.I. du Pont de Nemours & Co.). U.S. 2,257,389, Sep. 30. Chemcial Abstracts, vol. 36, p. 99.
USPTO CNIDR, U.S. Patent 4,236,021, Nov. 25, 1980, Abstract for "Process for the manufacture of levulinic acid and esters".
Levulinic Acid as a Basic Chemical Raw Material, Reid H. Leonard, Industrial and Engineering Chemistry, vol. 48, No. 8, Aug. 1956, pp. 1330–1341.
Takahashi, J. Agr. Chem. Soc. Japan, vol. 20, 1944, pp. 553–556.
Database WPI: Section Ch. Week 9439: Derwent Publications Ltd., London, GB; Class B02, AN 94–315178; XP002060828 & SU 1 817 770 A (AS SIBE Chem Techn Inst Org Materials); May 23, 1993.
Effect of heat on aqueous solutions of sucrose and other carbohydrates. R. Montgomery and L.F. Wiggins, J. Soc. Chem. Ind. 66, 31–2 (1947); Chemical Abstracts, vol. 41, Col. 4025.
Interpretation of some reactions in the carbohydrate field in terms of consecutive electron displacement. Horace S. Isbell, J. Research Natl. Bur. Standards 32, 45–59 (1944); Chemical Abstracts, vol. 38, Col. 2319.
Thermochemical Pretreatment of Lignocellulose to Enhance Methane Fermentation: I. Monosaccharide and Furfurals Hydrothermal Decomposition and Product Formation Rates. K. Baush and P. McCarty, Biotechnology and Bioengineering, vol. 31, pp. 50–61 (1988).

*Primary Examiner*—Bernard Dentz
*Attorney, Agent, or Firm*—Knobbe, Martens, Olson & Bear, LLP

[57] ABSTRACT

A method of producing dehydration products from one more 5-carbon or 6-carbon sugars includes reacting said one or more sugars at 40–240° C. for 1 to 96 hours in the presence of 5–90% sulfuric acid, separating the reaction products, and recovering levulinic acid. The sugars are can be generated from strong acid hydrolysis of biomass, such as rice straw, paper, cotton and other cellulosic materials.

38 Claims, 2 Drawing Sheets

METHOD FOR THE PRODUCTION OF LEVULINIC ACID AND ITS DERIVATIVES

RELATED APPLICATION

This application is a continuation-in-part of U.S. patent application Ser. No. 08/747,441, filed Nov. 8, 1996 now U.S. Pat. No. 5,892,107.

FIELD OF THE INVENTION

The present invention relates to a method of producing levulinic acid from sugars in the presence of concentrated acid. In addition, the invention relates to a method for producing methytetrahydrofuran from the levulinic acid thus obtained. These novel methods can utilize waste biomass as the starting material for the levulinic acid and its numerous derivatives, thus adding to the economic viability of the invention.

BACKGROUND OF THE INVENTION

Levulinic acid is a major product of the controlled degradation of sugars by acid hydrolysis. Although levulinic acid has been known since the 1870's, it has never attained much commercial significance. One of the reasons for its slow development is the cost of the raw materials for synthesis. Another reason is the low yields of levulinic acid obtained from most synthetic methods. These low yields are largely due to the inherent physical properties of levulinic acid which do not allow for its facile recovery. Moreover, the production of levulinic acid has had high associated equipment costs. Given these factors, therefore, the production of levulinic acid has not appeared to be commercially feasible.

Despite the inherent problems in the production of levulinic acid, however, the reactive nature of levulinic acid makes it an ideal intermediate leading to the production of numerous useful derivatives. Levulinic acid, therefore, is desirable as a basic chemical raw material. See R. H. Leonard, "Levulinic Acid as a Basic Chemical Raw Material," *Industrial and Engineering Chemistry*, Vol. 48, p.1331–41 (1956).

The formation of levulinic acid from low-cost cellulosic material could, however, overcome one of the major difficulties encountered in other synthetic processes. By starting with waste biomass the cost of the starting material for production of levulinic can be greatly reduced. Moreover, the supply of sugars from cellulose-containing plant biomass is immense and replenishable. Most plants contain cellulose in their cell wall. For example, cotton is 90% cellulose.

Furthermore, it has been estimated that roughly 75% of the approximate 24 million tons of biomass generated on cultivated lands and grasslands is waste. This cellulose that is derived from plant biomass could be a suitable source of sugars to be used in the process of obtaining levulinic acid. Thus, the conversion of such waste material into a useful chemical, such as levulinic acid, would be desirable.

Sugars are converted to levulinic acid essentially by a process of dehydration and cleavage of a mole of formic acid. See Reid H. Leonard, supra. The literature in the art suggest that levulinic acid can be formed quite readily from glucose and other sugars by the action of boiling the sugars in a dilute acid solution. See P. T. Sah and S. -Y. Ma, "Levulinic Acid And Its Esters," *J. Amer. Chem. Soc.*, 52:4880 (1930); and L. Fieser and M. Fieser, "Reagents for Organic Synthesis," John Wiley and Sons, Inc. 1967, p. 564–66.

In the literature concerning production of levulinic acid from sugars, however, generally HCl is used as the acid source in the dehydration reaction of sugars. See L. Fieser and M. Fieser, supra.; Alva Thompson, U.S. Pat. No. 2,206,311; Wendell W. Moyer, U.S. Pat. No. 2,270,328; Georg Scheuing and Wilhelm Konz, U.S. Pat. No. 2,305,738; Walter N. Haworth and Leslie F. Wiggins, British Patent No. 583,533. Sulfuric acid has been used as the acid source in dehydration reaction of bran, the here the reported product is furfural, rather than levulinic acid. See Paul Karrer, "Organic Chemistry," 2nd ed, Elsevier Publishing Co, Inc., New York 1946, p.737.

The theoretical yield of levulinic acid from a hexose is 64.5%. The literature in the art, however, indicates that only about two-thirds the theoretical yield can be attained in the presence of dilute HCL. Interestingly, substantially the same yields were obtained from cellulose in Douglas fir sawdust. See Reid H. Leonard, supra. Thus, it appears possible to utilize cellulosic materials to produce sufficient quantities of levulinic acid to be used as a basic raw chemical material.

If a low-cost production of levulinic acid could be achieved, such as the formation of levulinic acid from low-cost cellulosic material, the useful derivatives of this chemical are numerous. For example, esters of levulinic acid are used for flavoring, and some have been reported to be used as plasticizer. Reaction of levulinic acid with carbonyl reagents also can yield numerous derivatives, many of which are hydrazones and semicarbazones. These derivatives are of interest for conversion into pyridaziones and for the preparation of soluble derivatives of insoluble, but biologically active, materials. Also alkyl metal halides react with levulinate esters to yield a series of γ-substituted γ-valerolactones, some of which may be used for perfumes and flavors.

Oxidation products of levulinic acid are also known. These include the peroxide, methyl vinyl ketone, and succinic, malonic, and acetoacrylic acids. These derivatives have been postulated to be of use in foods, and as solvents in liquid-liquid extractions of hydrocarbons. In addition, the 4-amino derivatives of levulinic acid readily forms lactams and 5-methylpyrrolidones, while the amides upon hydrogenation of the keto group, also form 5-methylpyrrolidones.

Upon distillation, dehydration of levulinic acid occurs and α-angelica lactone (γ-lactone of 4-hydroxy-3-pentenoic acid) is formed together with some β-angelicalactone (γ lactone of 4-hydroxy-2-pentenoic acid). Various heterocyclic compound are also derived from levulinic acid. Some of these are pyrones, dioxanes, a coumarin, and thiazocines, which have been proposed for use as bacteriostatic and analgesic agents.

Moreover, substitution of levulinic acid for a portion of the acetyl groups in vinyl acetate-containing resins and cellulose acetate has been shown to yield materials of increased strength. The α-angelica lactones, one of the simplest products to be made from levulinic acid, can also be converted to a series of pseudolevulinic acid derivatives and has also been reported to be a means of obtaining 3-chloro-levulinic acid.

Reduction products of levulinic acid are also important. It has been reported that catalytic hydrogenation at temperatures above 200° C. yields substantial amounts of 1,4-pentanediol, and smaller amounts of α-methyltetrahydrofuran, and 1-pentanol. See Reid H. Leonard; G. Natta, R. Rigamonti and E. Beati, "The Hydrogenation of 2-furaldehyde And Its Derivatives," Chimica e Industria (Italy) 23, 117–23 (1941).

In all, the exceptional reactivity of levulinic acid and its lactones coupled with its availability from waste biomass provide an ideal set of conditions for the use of levulinic acid as a basic chemical raw material. Thus, there exists a need to be able to produce levulinic acid. Moreover, it would be most desirable to be able to produce levulinic acid in an economically viable and environmentally safe process.

SUMMARY OF THE INVENTION

The present invention is directed toward a method of producing levulinic acid and other derivatives, such as furfural, 5-HMF, succinic acid, maleic acid, fumaric acid, and methyltetrahydrofuran, from sugars.

In one aspect of the present invention, levulinic acid is produced by utilization of sugars produced by strong acid hydrolysis. The steps of this method include: 1) mixing biomass containing cellulose and hemicellulose with a solution of approximately 5–50% acid, preferably 10–30% acid, thereby decrystallizing the biomass, 2) heating the mixture to about 80–200° C., preferably 110–160° C., for 1 to 30 hours, preferably 2 to 10 hours, thereby hydrolyzing the cellulose and hemicellulose materials and causing the reaction of the resulting mixture of sugars to form the reaction products, 3) pressing or filtering to separating the liquid portions from the solid biomass portion, 4) separating the reaction products, and 5) recovering levulinic acid. It is noted that sulfuric acid is the preferred acid to be used in this method, and that the biomass used in the start of the reaction leading to levulinic acid can consist of rice straw, woody plant, paper, cotton, corn stalks, grass, bagasse, or other plant material. Both cellulose and hemicellulose can also be used as starting material when utilizing the method outlined above.

Preferably the above method is performed wherein the concentrations of the cellulose (within the preferred range of 12–39% percent by weight in the reaction solution) and acid (in percent by weight in the reaction solution) and the temperature are chosen according to the relation:

$$A = -0.4T30\ 70 - 0.59(C - 25.5)$$

wherein A is the concentration of sulfuric acid, T is the temperature in degrees Celsius, and C is the concentration of cellulose, wherein the value of A may deviate from the valve obtained from the equation by plus or minus 5% by weight in the reaction solution, the values of T may deviate by plus or minus 10° C. of the values obtained from the equation, and the values of C may deviate from the value obtained from the equation by plus or minus 5% by weight in the reaction solution. Preferably, the biomass concentration is 20–40%, more preferably 30%.

The production of levulinic acid via the above process also allows for recovery of products selected from the group consisting of furfural, 5-HMF, succinic acid, maleic acid, fumaric acid. These products along with levulinic acid and sulfuric acid can be separated by chromatography, preferably using an ionic resin. However, it is more preferred that the separation be effectuated using an anionic resin, and most preferably the resins would also consist of multiple chromatographic columns.

In another aspect of the present invention, the levulinic acid obtained from either of the three methods outlined above can be used to form derivative products, such as methyltetrahydrofuran. The steps of this method include: 1) hydrogenation of the levulinic acid in the presence of $H_2$ and a metal catalyst, 2) separating the reaction products, and 3) recovering methyltetrahydrofuran. This hydrogenation reaction can also be conducted in the presence of added ethanol, either in a wet or in a dry form. The methyltetrahydrofuran product can be dried after the hydrogenation reaction, leaving the resulting product in a dry blend form. The preferred metal catalyst to be used in the hydrogenation reaction of levulinic acid is a Ni/Co catalyst. Also, it should be noted that if the levulinic acid is dried subsequent to its production, the resultant product is angelica lactone, due to dehydration of the levulinic acid.

In utilizing the above-outlined method of producing levulinic acid, it is preferred that the reaction products be filtered prior to separation. Additionally, it is preferable that the filter be washed one or two times, and that preferably these washes are to be combined prior to separation. Moreover, following separation of the reaction products, levulinic acid can be concentrated to facilitate any further reaction.

In yet another aspect of the present invention, when utilizing the above-outlined method, an alcohol can be added to the reaction mixture subsequent to the production of levulinic acid. The resultant reaction mixture is preferably run for 1–10 hours at the reaction temperature of the alcohol. The final reaction mixture can be separated to yield levulinate ester. Preferably the reaction time to produce the ester would be 2–8 hours with a reaction time of 3–6 hours being most preferred.

DETAILED DESCRIPTION OF THE INVENTION

Introduction

Figure 1:
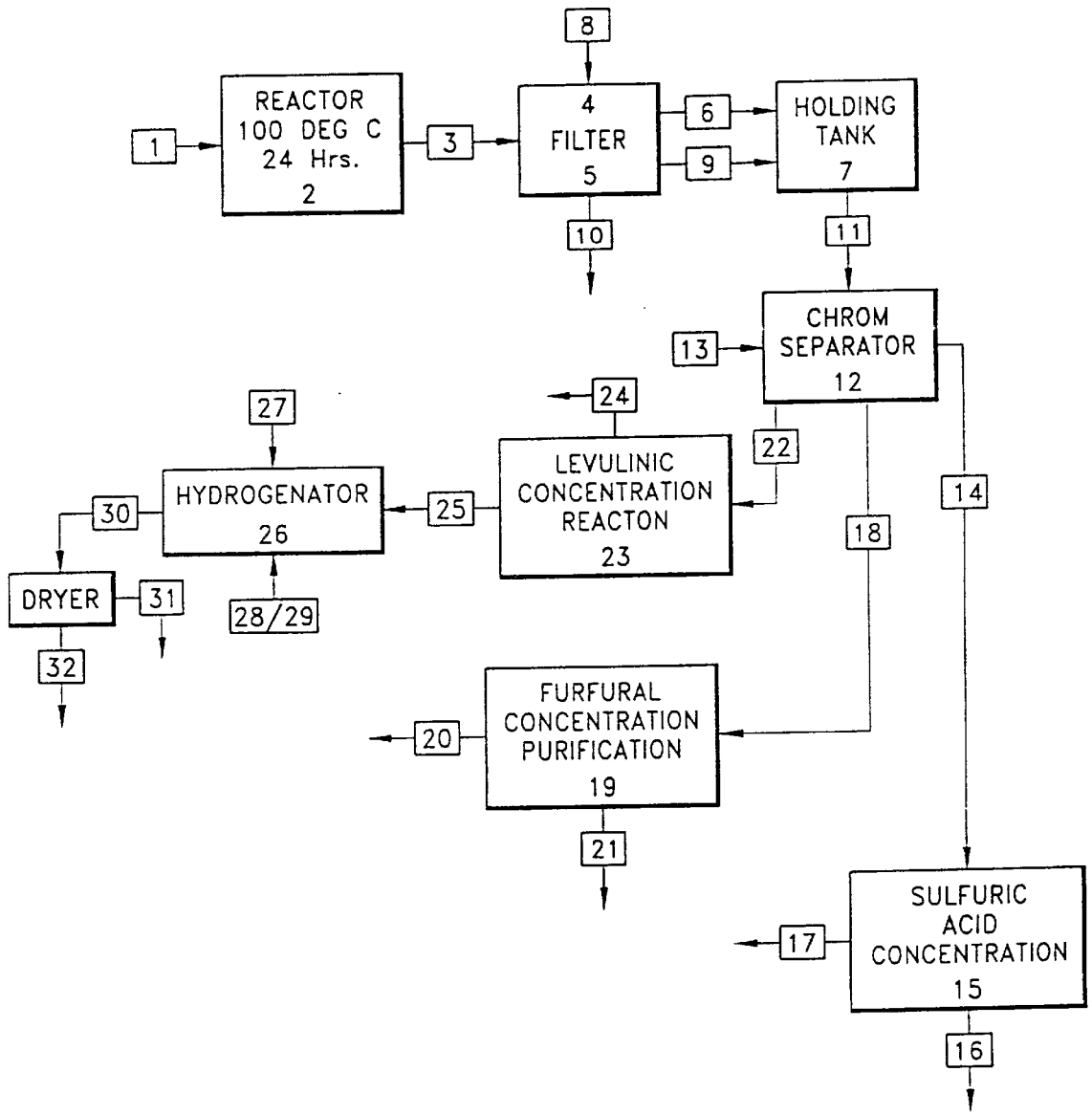
FIG. 1 is schematic view of the method of the present invention illustrating in a Product Flow Diagram the steps leading to the production of levulinic acid and tetramethylhydrofuran.

Recently, a successful process has been discovered that provides for strong acid hydrolysis of plant biomass consisting largely of cellulosic and hemicellulosic materials. See U.S. Pat. No. 5,526,777 ('777 patent), entitled "Method of Producing Sugars Using Strong Acid Hydrolysis of Cellulosic and Hemicellulosic Materials," and hereby incorporated by this reference thereto. This acid hydrolysis method results in a high yield of sugars as an intermediate in the process. Moreover, this acid hydrolysis process provides a means for producing sugars from biomass in a manner that reduces the amount of waste product of effluents produced.

Thus, the process of the '777 patent is designed to reuse all aqueous streams and to convert all solids to saleable or useful products. Much of the acid used is also recovered for recycling. Also where the biomass contains high levels of silica, the process is able to produce silica gel, sodium silicate, potassium silicate, zeolites, or other ancillary products. Moreover, a high yield of sugar is obtained form the hydrolysis of the biomass, making concentration of the sugar streams unnecessary for most subsequent processes.

Other features of the patented acid hydrolysis method contribute to its efficiency and economic feasibility in the production of sugars. These include the use of atmospheric pressure and relatively low temperatures. Moreover, the process does not involve the production of furfural and similar undesirable by-products which are toxic and also may inhibit subsequent reactions of the sugars thus obtained. Finally, this process does not require the use of exotic and expensive materials of construction such as tantalum steel.

Thus, the process of the '777 patent provides an efficient, cost-effective means of producing useful chemicals from the hydrolysis of agricultural waste, while at the same time producing little or not waste effluents or materials. Moreover, since the hydrolysis process produces a high yield of sugars, it would appear to be a suitable method for use in the production of useful derivatives from the sugar intermediate thus obtained. One such derivative could be levulinic acid.

The present invention provides an improved process for obtaining levulinic acid from sugar, as well as derivatives of levulinic acid, such as methyltetrahydrofuran(MTHF). Levulinic acid can be produced from sugars derived from cellulose and hemicellulosic materials, as detailed in the '777 patent and incorporated herein by reference, or from sugars derived from other sources. It should be noted, however, that although the strong acid hydrolysis process described in the '777 patent, provides an efficient means of producing sugars from biomass to be used subsequently in the method of the present invention, this method represents only one route to obtain raw sugar to be used as starting material in the disclosed invention. The novel method of the present invention leading to levulinic acid can utilize any sugar component as a starting material, regardless of whether the sugar is mixed, a combination of 5-carbon and 6-carbon sugars, exclusively contains 5-carbon or 6-carbon sugars, or is obtained from biomass by methods other than that described in the '777 patent.

If the method detailed in the '777 patent is utilized to obtain sugar, the hydrolysate will generally include the 6-carbon sugars (C6) glucose, mannose and galactose and the 5-carbon sugars (C5) xylose and arabinose. The hydrolysate mixtures formed in the method of the '777 patent primarily consist of glucose and xylose with small amounts of the other sugars. However, where cellulose is used as the starting material in the process, such as that of recycled paper, the exclusive product is glucose. Additionally, in situations where the biomass has increasing amounts of hemicellulose, the entire range of C6 and C5 sugars is produced.

The present invention discloses a novel method to produce dehydration products of sugars, such as levulinic acid (LA), furfural, 5-hydroxymethyl-2-furanone (5-HMF), maleic acid (MA), succinic acid (SA), and fumaric acid (FA), even if the starting components consist of mixed sugars. The present invention also allows for the selection of conditions that can alter the product ratio so that economic flexibility can be incorporated into the production of these dehydration products.

In addition, the method of the disclosed invention provides steps to prepare high yields of the dehydration products and to prepare the products that all process streams are reusable, after the recovery of the desired products. Moreover, the present invention allows for these dehydration products to be produced in high yield in economically viable and environmentally safe processes. Finally, the invention also discloses the method of preparation of derivatives of levulinic acid by hydrogenation yielding methyltetrahydrofuran (MTHF).

There are numerous advantages to the present invention. These include the following:

1. A mixed C6-C5 acid stream can be used without the need for separating the sugars;
2. The yields of levulinic acid and its derivative, MTHF, are significantly higher than other known methods, in part due to the high concentration of sulfuric acid which was discovered to act as a dehydration catalyst at the concentrations utilized in the present invention;
3. The concentration of sulfuric acid remains high throughout the reaction and subsequent separation, thus facilitating its recovery for reuse;
4. The product mix can include products which become intermediates to the common final product;
5. The invention allows for the recycle and reuse of all streams, and any unwanted byproducts can be subsequently oxidized to non-toxic materials.

This last advantageous aspect of the invention is significant when sulfuric acid is used in the process because the presence of this acid will degrade and oxidize products if not removed. For example, $H_2SO_4$ degrades formic acid, which is formed as a necessary by-product in the dehydration reactions.

FIG. 1 shows a Product Flow Diagram indicating the overall steps leading to the production of levulinic acid and/or MTHF. This Product Flow Diagram is illustrative of a preferred embodiment. All streams are indicated by arrows with the overall steps being illustrated by the larger boxes to which the product streams are directed.

First the sugar (1) is fed into the reactor (2). The sugar can be derived from the process of strong acid hydrolysis, as detailed in the '777 patent, or can be any sugar, either a mixed sugar, consisting of both 6-carbon and 5-carbon sugars, or exclusively a 6-carbon or 5-carbon sugar. Next the reaction mixture is heated at 80–120° C. for 7 to 42 hours. Preferably the reaction of the sugars in concentrated sulfuric acid is carried out at 100° C. for 24 hrs. When the method detailed in the '777 patent is used, the concentration of sulfuric acid will be in the range of 25–39%, without further addition of acid. If the sugar source is not from that of the strong acid hydrolysis method, however, sulfuric acid is added to the reactor to a final concentration of approximately 30–39%.

Next the resulting product mixture (3) is transferred to a filtration system (4), where an initial cake (5) is formed. The first filtrate (6) is then transferred to the holding tank (7). The cake is subsequently washed with $H_2O$ (8), resulting in a second filtrate (9) which is also transferred to the holding tank. After the $H_2O$ wash, the cake discharge (10) can be removed from the filter.

The combined filtrates (11) are then applied to the chromatographic separator (12), where the products of the reaction as well as sulfuric acid can be separated. The products are separated by $H_2O$ (13) feed into the separator. Preferably the resin utilized in the chromatography is an anionic resin, for which sulfate ions form the anionic state. Most preferably, a system of multiple chromatographic columns, referred to in the art as "simulated moving bed chromatography," can be utilized to effect the initial separation; the use of multiple chromatographic columns permits the removal of products, addition of further eluents, or recycles between columns.

Figure 2:
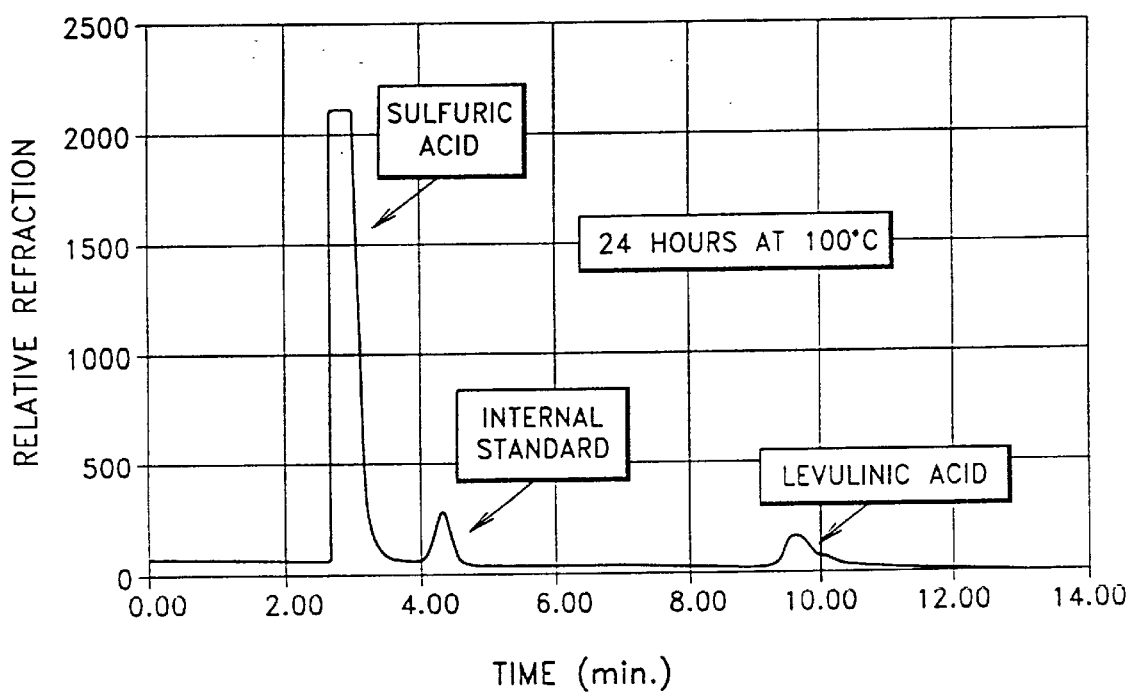
FIG. 2 represents the relative refractive index of the products as a function of time of elution from the chromatographic system.

FIG. 2 shows a typical chromatograph of the separation after reaction for 24 hrs at 100° C., where levulinic acid is the primary product. This chromatograph was generated using a Dynamax™ $NH_2$ 83-701-C column, which is provided prepacked with a weak anion amine resin and is available from Rainin of Woburn, Mass. As FIG. 2 illustrates, sulfuric acid can be cleanly separated from the levulinic acid product. This allows the strong acid to be recycled for reuse, and thus, adding to the economic viability of the process. Under these conditions, succinic, maleic and fumaric acid can also be separated.

The following sets forth one exemplary set of specific separation conditions:

A 24" long, 2" in diameter column was loaded with Mitsubishi A306S anionic resin to a bed volume of 1 liter.

75 ml of levulinic acid/sulfuric acid mixture (5% levulinic acid and 30% $H_2SO_4$) was fed onto the column and eluted with $H_2O$. Levulinic acid eluted from the column after approximately 24.5 minutes with the sulfuric acid eluting at approximately 28 minutes. With an application of only 50 ml, the levulinic acid still eluted at approximately 24.5 minutes, while the sulfuric acid eluted at approximately 29.75 minutes. It is important that these separation condition yield enough of a difference in the elution profile of the products to be utilized on a moving bed commercial chromatographic separation system. Moreover, it appears that the separation can proceed using a cationic resin as well.

Another example of a particular separation procedure is as follows:

A 24" long, 2" in diameter column was loaded with Dow XFS-43254.00 anion resin to a bed volume of 1 liter. 100 ml of levulinic acidisulfuric acid (5% levulinic acid and 30% $H_2SO_4$, was fed to the column eluted with $H_2O$. Levulinic acid eluted at approximately 22.75 minutes, and the sulfuric acid eluted at approximately 40 mintues. In this example, there was total separation, with no overlap of the peaks, thus indicating that this procedure could be used to give an effective separation even in the absence of simulated moving bed techniques. However, the moving bed chromatographic techniques are preferred because higher concentrations could be maintained throughout the separation.

Following the chromatographic separation, sulfuric acid (14) is feed into an acid concentrator (15) leading to the removal of $H_2O$ (16) and concentrated $H_2SO_4$ (17) being available for reuse at the initial stage of the strong acid hydrolysis process. Furfural (18), along with 5-HMF, can also be separated by the chromatography method described above, eluting from the column after the sulfuric acid component of the reaction mixture. The furfural containing eluent can then be further concentrated and purified (19), leading to furfural product (20) and $H_2O$ (21).

The final eluent from the chromatographic separator is levulinic acid (22) in $H_2O$ with a small amount of acid. The product can be further concentrated (23) by evaporation of $H_2O$ (24) prior to the hydrogenation reaction, leaving levulinic acid product containing a small amount of acid. Advantageously, the acid present serves as a catalyst, thus obviating the need to add acid at this point. Once the $H_2O$ is removed, the temperature is increased to 150° C., and a vacuum is applied at 10 torr. Thus, various forms of isomers of angelica lactone (25) can be formed, which can be collected and used in the hydrogenation reaction.

One use of the levulinic acid obtained is to hydrogenate the product to MTHF. If MTHF is desired as an end product, angelica lactone isomers are transferred to the hydrogenator (26), along with $H_2$ (27), ethanol (28), and the Ni/Co catalyst (29). This mixture is reacted in the hydrogenation reactor at a pressure of 750–3000 psig, until there is no remaining $H_2$ uptake. Preferably, the temperature of the reaction would be at 50° C. to at temperature below the decomposition temperature of the lactone, which is approximately at 200° C. The product, MTHF (30), can then be transferred to a liquid or vapor phase dryer unit to remove $H_2O$ (31), also making using of a desiccant or absorbent. The final MTHF product is now in a dry blend form (32). Moreover, the production of a mixed stream in this case, that is MTHF and ethanol, would have an advantage over current technology in the finished mixtures can be made more economically than making the products separately, and then blending the finished products for use.

It should also be noted that in many instances it is more economically sound to insert an separation step in the midst of the levulinic formation at the site of the primary reactor, so that product of value can be immediately extracted. Thus, it may be undesirable to wait 7–42 hours to extract the products. For example, in this dehydration reaction, as time proceeds furfural is converted into succinic, maleic, and fumaric acids. If furfural was a desired product, it would be preferred to do an initial separation early in the reaction, and then, sending the remainder back to the reactor for completion of the levulinic acid reaction.

It is noteworthy that the dehydration reaction produces different products as the time of reaction is increased. At 100° C., the reaction of the 6-carbon sugars will go through 5-HMF yielding levulinic acid, whereas the reaction of 5-carbon sugars will go through furfural to yield succinic, maleic, and fumaric acids. However, literature in the art indicate that these reactions may not be exclusive, in that a intermediate product of the reaction with 6-carbon sugars may be a 5-carbon sugar production, and vice versus. Ojota et al. *J. Pharm. Pharmac.*, 30:668 (1978). In addition, Great Lakes Chemical have a chemical process of making MTHF from furfural alcohol, by starting with 5-carbon sugars and resulting in furfural.

Moreover, it is generally hypothesized that the synthesis of levulinic acid requires the simultaneous oxidation of aldehydes, as a source of hydrogen, resulting a reduced form of levulinic acid. Thus, if mixed sugars are used in the reaction, the overall yields can be improved because the degradation products of the 5-carbon sugars, for example, the aldehydes produced, act as appropriate reducing agents for the reaction, leading to higher yields of levulinic acid from the 6-carbon sugars.

Although it is possible to write a balanced equation for the reaction of a 6-carbon sugar leading to one mole of levulinic acid, one mole of formic acid, and one mole of $H_2O$, the actual reaction mechanism is not completely known. The requirement of a saturated levulinic acid product, plus the unsaturated nature of 5-HMF, however, indicate that it is highly probable that more than one mole of 6-carbon sugar is required to yield a mole of levulinic acid. For example, Augh et al. showed polymerization of 5-HMF, thus reducing levulinic acid. Thus, the theoretical yield of 64% dictated by the simple balanced equation is never achieved. The reported yields are generally on the order of 20% of the theoretical yield, i.e. a yield of about 13%. There are only a few reported results; in one report, 150 g of product resulted from reaction of 1000 g of glucose with HCl, i.e. a 15% yield. This result was claimed to be an improvement over previous reported results. See Sah et al., supra.

In the present invention the actual yield of levulinic acid for the 7 hour reaction time was 23.3%, or 36% of the theoretical yield. This yield is approximately 50% higher than the reported literature value. See L. Fieser and M. Fieser, "Reagents for Organic Synthesis," John Wiley and Sons, Inc. 1967, p. 564–66. It is noteworthy that the 24 hour reaction yields approximately twice the reported yields.

Finally, analysis of the method of the present invention, indicate that all the sugar disappears from the reaction mixture between 7–24 hours after the reaction is initiated. These results also show an increase in 5-HMF as a function of decrease of the sugar levels in the reaction mixture. Levulinic acid is produced following the appearance of 5-HMF.

When the sugars from which the levulinic acid is produced are derived from cellulosic and hemicellulosic raw materials, the method described above results in the highest yield of product per pound of raw material. If, however, economic factors favor a process which is faster and requires less capital investment, an alternate method, described below, which is faster and requires fewer steps may be used. This alternate procedure is an integrated method wherein the sugar or sugar/acid stream is not recovered as an intermediate, and results in a slightly lower yield of levulinic acid per pound of raw material than that described above, but the yields are still higher than the previously reported literature values for yields.

The integrated procedure begins by mixing cellulosic and hemicellulosic raw materials, such as biomass or recycled paper, with acid, preferably sulfuric acid to form the reaction solution. The preferred concentrations of the components, as percent by weight in the reaction solution, are preferably about 20–40%, more preferably about 30% for the biomass; preferably 12–39%, more preferably 21–30% for the cellulose; and preferably 5–50%, more preferably 10–30% for the acid. When the acid and biomass are combined, decrystallization of the biomass occurs. The decrystallization is exothermic, so the temperature spontaneously rises as the components are mixed. The temperature should not be allowed to rise higher than about 40–60° C., otherwise the materials may degrade before significant conversion takes place. A reasonable temperature can be maintained by controlled addition of the raw materials or cooling the solution.

Once the decrystallization has taken place, the reactants are heated to 80–200° C., preferably 110–160° C., for a time of 1 to 30 hours, preferably 2 to 10 hours. Unlike the longer method described previously wherein the hydrolysis and reaction of the sugars are performed separately, in this method as the decrystallized materials hydrolyze to form sugars those sugars then react to form levulinic acid. Furthermore, all of this is done while the solution is in contact with the remaining solids. Once the reaction is complete, the resulting product mixture is processed according to the Product Flow Diagram beginning at step (3) and as described above.

The inventors have found that for a given amount of biomass in the reaction solution, if the temperature of the reaction is increased, the concentration of sulfuric acid must be decreased in order to maintain a high yield of levulinic acid. Similarly, if the temperature of the reaction is decreased, the concentration of sulfuric acid must be increased in order to maintain the high yield of levulinic acid. Through experimentation using paper as the biomass, the inventors found that the relationship between the concentration of sulfuric acid, concentration of cellulose, and the temperature may be approximated by the equation:

$$A = -0.4T + 70 - 0.59(C - 25.5).$$

wherein A is the percent sulfuric acid by weight in the reaction solution, T is the temperature in degrees Celsius, and C is the percent cellulose by weight in the reaction solution, which is preferably within the preferred range of 12–39% by weight in the reaction solution.

The series of reactions from which the equation was derived had concentrations of paper (85% cellulose) of 30% paper (25.5% cellulose) and 40% paper (34% cellulose) by weight in the reaction solution. These reactions also had sulfuric acid concentrations between 7.5% and 30% by weight in the reaction solution, and a temperature range of 110–160° C.

The equation given above approximates the conditions for achieving a high yield. The conditions used should deviate from those obtained from the equation by not more than 5% by weight in the reaction solution for the values obtained for A, not more than 5% by weight in the reaction solution for the values obtained for C, and not more than 10° C. of the values obtained for T. Greater deviations will likely result in either a lower yield or a slower reaction. For the deviations for A and C, if the value obtained from the equation is 20, meaning 20% by weight in the reaction solution, the conditions used should lie within the range of 15 and 25% by weight in the reaction solution. The results from one of the experiments using 25.5% cellulose (30% paper) from which the above equation was derived is shown in Table 1 below. The percent levulinic acid (% LA) values correspond to the molar percent conversion of levulinic acid compared to the theoretical conversion, which in the case of conversion of cellulose to levulinic acid is 71.5%.

TABLE 1

REACTION CONDITIONS AND RESULTS
FOR 25.5% CELLULOSE FROM PAPER

| Acid Concentration | Temperature (° C.) | | | | | |
|---|---|---|---|---|---|---|
| | 160 | 150 | 140 | 130 | 120 | 110 |
| 30% | | 16.4% LA 3 hrs | | | 47.1% LA 4 hrs | 29.6% LA 6 hrs |
| 25% | 28.0% LA 6 hrs | | | 32.9% LA 9 hrs | 56.1% LA 9 hrs | |
| 20% | | | 40.5% LA 4 hrs | 45.0% LA 3 hrs | | |
| 15% | 47.3% LA 3 hrs | 45.5% LA 5 hrs | 37.3% LA 6 hrs | | | |
| 10% | 59.8% LA 8 hrs | | | | | |
| 7.5% | | | | | | |

The reactions having a concentration of cellulose of about 25.5% by weight were generally found to than those having the concentration of cellulose at 34%. This may be seen by the results presented in 2 below. In Table 2, as in Table 1 above, the percent levulinic acid (% LA) values correspond to the molar percent conversion of levulinic acid compared to the theoretical conversion.

TABLE 2

CONDITIONS AND RESULTS
USING PAPER AS BIOMASS

| % paper | % cellulose | % sulfuric acid | temperature | time (hrs) | yield (% LA) |
|---|---|---|---|---|---|
| 30 | 25.5 | 10 | 150 | 8 | 59.8 |
| 30 | 25.5 | 15 | 150 | 3 | 47.3 |
| 30 | 25.5 | 15 | 140 | 5 | 45.5 |
| 40 | 34 | 10 | 150 | 4 | 33.7 |
| 40 | 34 | 15 | 150 | 6 | 38.2 |
| 40 | 34 | 15 | 140 | 4 | 43.6 |

A Method of Production of Levulinic Acid and Other Dehydration Products of Sugars Derived From Strong Acid Hydrolysis A method of strong acid hydrolysis of cellulose and hemicellulose is detailed in the '777 patent. This is a preferred method to derive sugars as starting material for the production of levulinic acid and its derivatives, as disclosed in the present invention. In the following examples, the hydrolysate was generally derived from rice straw. In addition, to present examples that illustrate the reaction under varying conditions, 5-carbon and 6-carbon sugar were added to modify the ratio present in the hydrolysate.

After the conventional hydrolysis step of the '777 patent, there are two points in this process where chemistry can be performed. Moreover, either the mixed sugar stream, which is the first hydrolysis stream, or second hydrolysis stream consisting of virtually all glucose can be selected for use in subsequent chemical reactions. (See FIG. 1 of the '777 patent). Of course, these two streams can be combined yielding mixed sugars as starting material in further reactions.

The two points in the acid hydrolysis process where additional chemistry can be performed are: 1) immediately after the belt pressing step (See FIG. 1 of the '777 patent) or 2) immediately after the acid/sugar separator step, where sulfuric acid is removed from the sugar residue (See FIG. 2 of the '777 patent).

After Pressing

After the first hydrolysis step, the sugar concentration is approximately 15%, while the acid concentration is approximately 30%. It is this stage of the strong acid hydrolysis process that appears to be ideal for optimization of dehydration reactions leading to levulinic acid, furfural, 5-HMF, and other degradation products of these primary products, succinic, maleic and fumaric acids. Following the reaction of the sugar/acid mixture, leading to the desired product(s), the products can be separated from the acid component via chromatography, as described in the above Product Flow Diagram.

The advantage of proceeding via this route is that the strong acid hydrolysis method produces sugars in high yields in a convenient part of the raw material concentration scheme, as described in the '777 patent. Another advantage is that reactions can be carried out with only minimal purification of intermediates products. Thus, final purification can be done later in the regime after products of high value have been obtained.

It was also discovered by experimentation that sulfuric acid does not proceed via same the mechanism as HCl, which is the acid generally used in the art to produce dehydration products of sugars, such as levulinic acid. An original experiment was performed where a solution of 10% glucose, by weight, was reacted in the presence of 1%, by weight, for 24 hours at 100° C., as described in the literature. See P. T. Sah and S. -Y. Ma, "Levulinic Acid And Its Esters," J. Amer. Chem. Soc., 52, 4880 (1930); L. Fieser and M. Fieser, "Reagents for Organic Synthesis," John Wiley and Sons, Inc. 1967, p. 564–66. After essentially following literature reaction conditions, except that $H_2SO_4$ was used instead of HCl, there was virtually no sugar degradation and no production of levulinic acid.

A similar reaction was also performed in which a solution of 3% $H_2SO_4$ and 10% glucose was reacted at 100° C. for 24 hours. In this case, the glucose decreased to 7.34% with a significant production of 5-HMF, but only insignificant amounts of levulinic acid. Here 0.058% of levulinic acid was produced, in sharp contrast to the reported yields in the presence of HCl. It should be noted that in substituting $H_2SO_4$ for HCl, the difference in acidic value of each acid was taken into consideration. Thus, a 6% solution of HCl is approximately equivalent to a 3% solution of $H_2SO_4$. These unanticipated results indicate that the mechanism of acid action is different with $H_2SO_4$ rather than HCl. Moreover, these surprising data lend support to use of the hydrolysate generated in the strong acid hydrolysis method of the '777 patent. The advantage of using this hydrolysate are many. It is produced at high concentrations in the first part of the '777 method, it contains high concentrations of $H_2SO_4$ which are necessary to get significant quantities of levulinic acid, or other dehydration products, and finally, purification steps are eliminated until the desired products are obtained.

EXAMPLE 1

Production of Levulinic Acid

A mixture of 5-carbon sugars, primarily xylose, 6-carbon sugars, primarily glucose, and $H_2SO_4$ were reacted in $H_2O$. The concentration of mixed sugars was 10–22%, by weight, the inorganic acid was 25–39% by weight, with the remainder being $H_2O$. This sugar mixture was prepared by the strong acid hydrolysis method by:

1) mixing materials cellulose and hemicellulose with a solution of approximately 25–90% of $H_2SO_4$, by weight, thereby at least partially decrystallizing the biomass and forming a gel that includes a solid and liquid portion;

2) diluting the gel thus obtained to an acid concentration of approximately 20–30% by weight and heating the gel to about 80–100° C., thereby hydrolyzing the cellulose and hemicellulose materials (first hydrolysis step);

3) separating the liquid portion from the solid portion, thereby obtaining a first liquid containing a sugar/acid mixture;

4) mixing the separated solid portion with a solution of about 25–90% $H_2SO_4$ by weight until the acid concentration of the resulting gel is between 20–30%, by weight, and then heating the mixture to temperature of 80–100° C., thereby further hydrolyzing the cellulose and hemicellulose materials remaining in the separated solid portion (second hydrolysis step);

5) separating the resultant liquid portion form the solid portion, and thereby obtaining a second liquid containing a sugars/acid mixture;

6) combining the first and second liquids.

The above liquid mixture is then heated at approximately 80–120° C. for about 7–42 hours, depending on the product ratio desired. It is preferable, however, that the reaction temperature be approximately 100° C. The dehydration products formed are levulinic acid, 5-HMF, furfural, succinic acid, maleic acid, and fumaric acid.

The product stream is then separated into component liquid streams containing the desired combination of products, or the individual products, and a separate stream which contains the inorganic acid, as illustrated in the Product Flow Diagram. The organic product streams each contain less that 3% sulfuric acid, and the inorganic stream contains less than 3% organic product. The inorganic stream can be concentrated to facilitate reuse of the sulfuric acid.

The organic products are further purified by conventional means resulting in the removal of $H_2O$, inorganic acid and minor impurities. For example, furfural is purified by a second distillation, which follows azeotropic distillation of the furfural/$H_2O$ mixture. Levulinic acid can be further purified by first by distilling the product followed by vacuum distillation. If necessary, recrystallization of the levulinic acid product can also be performed.

EXAMPLE 2

Production of Levulinic Acid

A mixture of 5-carbon sugars, primarily xylose, 6-carbon sugars, primarily glucose, and $H_2SO_4$ were reacted in $H_2O$. The reaction conditions consist of heating the mixture at a temperature of 80–120° C. for 7–42 hours, depending on the desired product ratio of levulinic acid, 5-HMF, furfural, maleic acid, succinic acid and fumaric acid. Preferably the reaction would proceed at 100° C. for 24 hrs. The concentration of mixed sugars were 10–22%, by weight, the inorganic acid was 25–39% by weight, with the remainder being $H_2O$. After production of the dehydration products, the reaction mixture is separated and purified as described in the Product Flow Diagram of FIG. 1. This mixture was prepared by the strong acid hydrolysis method by:

1) mixing materials containing cellulose and hemicellulose with a solution of approximately 25–90% of $H_2SO_4$, by weight, thereby at least partially decrystallizing the biomass and forming a gel that includes a solid and liquid portion;

2) diluting the gel thus obtained to an acid concentration of approximately 20–30% by weight and heating the gel to about 80–100° C., thereby hydrolyzing the cellulose and hemicellulose materials (first hydrolysis step);

3) separating the liquid portion from the solid portion, thereby obtaining a first liquid containing a sugar/acid mixture;

4) mixing the separated solid portion with a solution of about 25–90% $H_2SO_4$ by weight until the acid concentration of the resulting gel is between 20–30% by weight, and then heating the mixture to temperature of 80–100° C., thereby further hydrolyzing the cellulose and hemicellulose materials remaining in the separated solid portion (second hydrolysis step);

5) separating the resultant liquid portion from the solid portion thereby obtaining a second liquid containing a sugar/acid mixture;

6) heating this second liquid mixture at a temperature of approximately 80–120° C. for about 7–42 hours, depending on the desired product ratio, thereby forming primarily levulinic acid, 5-HMF, furfural, succinic acid, maleic acid, and fumaric acid;

7) separating this resulting third liquid, containing levulinic acid, 5-HMF, furfural, succinic acid, maleic acid, and fumaric acid, from the solid portion.

8) treating the first liquid stream with heat at approximately 80–120° C., preferably at 100° C., for about 7–24 hours, depending on the desired product ratio;

9) the reaction mixture now contains levulinic acid, 5-HMF, furfural, succinic acid, maleic acid, and fumaric acid, which is then combined with the third liquid containing the similar products thereby forming a single product stream;

10) the resultant product stream is then separated into component liquid streams containing the desired combinations of products or the individual components, and a separate stream containing sulfuric acid, as detailed in the above Product Flow Diagram;

11) the organic products are concentrated by removal of $H_2O$, and purified to remove residual inorganic acid and minor impurities by adjusting the pH with lime, in the case of $H_2SO_4$ removing $SO_4^{-2}$ ions.

EXAMPLE 3

Production of Levulinic Acid

In this example, the raw materials consist of only cellulose. This example is modification of examples 1 and 2 in which a solution of levulinic acid is first prepared by mixing material containing cellulose with a solution of sulfuric acid that is 25–90% acid by weight. This initial step allows for partial decrystallization of the cellulosic materials.

A gel is then formed that includes a liquid and solid portion. Next the gel is diluted to yield an sulfuric acid concentration of about 20–30% by weight. The gel is then heated to a temperature between 80–100° C. for a time interval of 45 minutes to 2 hours. This step hydrolyses the cellulose.

The liquid is further heated at temperature ranging from 80–120° C. for approximately 7–42 hours, depending on the desired product ratio. Two portions again form: a liquid portion and a solid portion. The primary product of this reaction, however, is levulinic acid, which is contained in the final liquid portion following the reaction.

The product stream is then separated into component liquid streams containing the desired combination of products, or the individual components. The inorganic acid is contained in a separate stream. Final purification of the organic products is performed as outlined in the above Product Flow Diagram.

EXAMPLE 4

Production of Levulinic Acid 700 grams of hydrolysate solution obtained from strong acid hydrolysis method detailed in example 1, which contained 15.5% sugars, mostly consisting of glucose, was heated for various times at 100° C. After seven hours, the reaction mixture contained 3.95% of levulinic acid.

EXAMPLE 5

Production of Levulinic Acid 120 gallons of hydrolysate from strong acid hydrolysis process, as described in example 1, containing approximately 1% by weight of glucose and residual degradation products of xylose, was placed in an acid concentrator to remove the residual $H_2O$ and concentrate the acid. After reacting at 100° C. for 24 hours, the reaction mixture was found to contain 0.3% levulinic acid. This example demonstrates the feasibility of producing levulinic acid as part of the routine acid recovery step in the strong acid hydrolysis process, given that the solution contains residual sugar.

EXAMPLE 6

Production of Esters of Levulinic Acid

It is possible to recover levulinic acid esters directly from the completed reaction as described in example 1. In this case, excess methyl or ethyl alcohol, that is, in stoichiometric excess to the amount of levulinic acid produced after the reactor step (see Product Flow Diagram), can be added to the levulinic acid/sulfuric acid mixture. The resulting mixture is refluxed for 3 hours forming the ester. The excess alcohol can then be distilled off the levulinate product. The levulinate ester can be recovered by phase separation, since it forms an oily layer atop of the aqueous layer. The ester product can also be separated from the sulfuric acid component, as well as from the excess alcohol, by the separation methods used for the levulinic acid product described above.

The following is example leading to the production of levulinate ester:

368 grams of a completed reaction solution from hydrolysate was used to form levulinate ester. In this case, the solution contained approximately 15.5 grams of levulinic acid and 110 grams of $H_2SO_4$. Next ethanol was added in excess. The resulting mixture was heated to ethanol reflux, approximately 80° C., for 3 hours. Following removal of the H$_2$SO$_4$ by chromatography, and removal of the remaining ethanol by distillation, approximately 15 grams of levulinate ester was recovered.

EXAMPLE 7

Production of MTHF

After the dehydration reaction of heating the sugars in concentrated sulfuric acid, as detailed example 1, the reaction mixture is then ready to be separated as illustrated in the Product Flow Diagram. The chromatographic separation is controlled to remove the sulfuric acid, and any of the succinic, maleic and fumaric acids that are produced in the dehydration reaction, while leaving the remaining products of levulinic acid, furfural and 5-HMF in a common aqueous solution. This aqueous solution is then concentrated by removal of H$_2$O.

Next the mixture is heated at approximately 150–175° C. under a vacuum of 1–50 mm Hg, which converts the levulinic acid to 5-methyl-2-furanone (5-M-2-F). The resulting mixture, containing 5-M-2-F, furfural, and 5-HMF into the hydrogenation reactor. Additionally, an ethanol solution in water, approximately 70–95% ethanol, is added to the hydrogenator reactor.

Water/ethanol is frequently used in hydrogenation reactions. In this example, the interaction of the MTHF product with ethanol allow for more facile drying and provides the product blended with solvent. The main reason, however, for the inclusion of ethanol in the hydrogenation reaction is that the MTHF product is highly flammable and known to produce explosive peroxides. This high volatile nature of MTHF does not generally permit it to be used or shipped without the addition of an inhibitor, such as butylated hydroxytoluene. In the disclosed hydrogenation reaction, inclusion of ethanol in the reaction, greatly reduces the risk of explosion associated with the production and use of MTHF product. Additionally, by the inclusion of ethanol in the entire process, including drying of the product, the risk of explosion further reduced.

The mixture is reacted with H$_2$ in the reactor in the presence of a suitable catalyst, preferably a Co/Ni catalyst. Hydrogen is added at an excess pressure of 750–3000 psig until there is no further H$_2$ uptake. Any residual H$_2$O is removed by azeotropic distillation or molecular sieve drying. The resulting product is an ethanol-MTHF blend which is ready for use or can be further separated into its two components.

It should be noted that although furfural can be hydrogenated in the presence of a Ni/Co catalyst, it is more difficult to hydrogenate than 5-HMF or 5-M-2-F. Thus, at the conditions specified for hydrogenation reaction of levulinic acid in the present invention, the entire mixture will be hydrogenated to yield MTHF. Moreover, the conditions for producing MTHF need to be selected for optimization of the reaction. If too much hydrogen pressure, or too high a temperature, is used, the reaction may go pass MTHF to yield 1,4-pentanediol instead.

EXAMPLE 8

Production of MTHF

The process of Example 7 is performed with the addition of dry ethanol rather than aqueous ethanol.

EXAMPLE 9

Production of MTHF

The process of Example 7 in which no ethanol is added to the hydrogenation reactor. In this example, the hydrogen pressure in the hydrogenation step is increased to approximately 2000–5000 psig.

After Sugar/Acid Separation

After the sugar and acid have been separated, which can be done after the first hydrolysis step, or after the second, the remaining concentration of acid is approximately 1%. This acid can either be left in the sugar mixture, or the acid can be converted to a salt which may be a suitable catalyst for the next chemical conversion, depending on the chemical route chosen.

Examples of additional chemical reactions that can be accomplished on the sugars after separation from the inorganic acid component include: 1) neutralization of the acid with sodium sulfate followed by electrolytic reduction to polyols; 2) air oxidation in the presence of sulfuric acid leading to difunctional acidic sugars; 3) neutralization of the sugar/acid mixture to a pH of 9.5–10.0 followed by air oxidation to monofunctional acidic sugars.

In is important that in both experimental approaches, either using the hydrolysate immediately after pressing, or by first putting the hydrolysate through the acid/sugar separation process, the critical purifications would be delayed until the value of the desired products are at their highest value for recovery. Thus, purification can be delayed until the production of the final products. If needed, an initial separation and purification of final products can be accomplished by the separation method described in the Product Flow Diagram of FIG. 1. Final purifications steps can be achieved in the conventional manner.

Exemplary Method of Production of Levulinic Acid by the Integrated Process

The following examples sets forth the techniques to produce levulinic acid and other products from a cellulose and hemicellulose material wherein the sugar or sugar/acid stream is not recovered as an intermediate. Although these methods are presented here, the levulinic acid produced by this method may be used in any of the procedures described herein which use levulinic acid to form other products.

EXAMPLE 10

Production of Levulinic Acid

A mixture of papers, predominantly newspaper but containing small amounts of plastic, glossy paper and cardboard, with a cellulose content of 85% was chosen as the raw material. Paper was added slowly to a solution of sulfuric acid in a 20 gallon glass-lined pressure vessel so as to keep the temperature of the mixture at or below about 40° C. This may also be accomplished by cooling the reaction vessel, or by a combination of slow addition and cooling. The concentration of sulfuric acid in the final solution was 10% by weight and the concentration of the cellulose by weight in the reaction solution was 25.5% (30% paper by weight).

After about 1.5 hours, the decrystallization was complete, and the mixture was then heated. It took approximately one hour to heat the mixture to the reaction temperature of 150° C. The time to achieve the reaction temperature is a function of the equipment and quantities involved; it is not a critical parameter in the process. Once the mixture was at the reaction temperature, the temperature was maintained for 8 hours. The mixture was then filtered to remove the solids and the product stream separated into component liquid streams, as outlined in the Product Flow Diagram above. The reaction produced 10.9% levulinic acid or 59.8% of the theoretical yield of levulinic acid from the quantity of cellulose in the paper.

EXAMPLE 11

Production of MTHF

The process of Example 7 was performed, using the reaction mixture from Example 10 in place of the mixture from Example 1. Examples 8 and 9 can also be performed similarly.

EXAMPLE 12

Production of Esters of Levulinic Acid

This method proceeds like that in Example 6, except the procedure of Example 10 is used to produce levulinic acid is performed and the mixture is filtered. Excess methyl or ethyl alcohol, that is, a stoichiometric excess to the amount of levulinic acid produced, can be added to the levulinic acid/sulfuric acid mixture. The resulting mixture is refluxed for about 3 hours forming the ester. The excess alcohol can then be distilled off the levulinate product. The levulinate ester can be recovered by phase separation, since it forms an oily layer atop of the aqueous layer. The ester product can also be separated from the sulfuric acid component, as well as from the excess alcohol, by the separation methods used for the levulinic acid product described above.

Exemplary Methods of Production of Levulinic Acid from Sugars

The following examples set forth specific techniques of the production of levulinic acid from different sugar mixtures:

EXAMPLE 13

The solution of 3% xylose, 12% glucose and 30% sulfuric acid was heated for various times at 100° C. The quantity of the total reactants was 500 grams. After 7 hours there was no sugar left and the levulinic acid concentration was 1.1%. By 16 hours, the levulinic acid had increased to 2.6%; and at 24 hours, the levulinic acid concentration was 4.2%. The final absolute yield of levulinic acid was 35% or 54% of the theoretical yield.

EXAMPLE 14

A solution of 12% glucose, by weight, and 30% $H_2SO_4$, by weight, was heated for various times at 100° C.±5° C. After 3 hours no significant levulinic acid was formed, however, the sugar had degraded to 4.49% along with significant production of 5-HMF. After 4 hours, the levulinic acid production was only 0.18% while the sugar had been reduced by approximately one-half of the 3 hour point. After a 7 hour reaction time, levulinic acid production was approximately 2.33%, and the sugar was reduced only slightly further. After 24 hours, there was not measurable sugar left, and the levulinic acid was now at 2.95%, or 46% of the theoretical yield.

Hydrogenation Reaction Leading to MTHF: Preparation of the Metal Catalyst

A typical hydrogenation catalyst can be prepared from Fe, Cu, Mn, Co, or Ni. Preferably, a mixture of Ni/Co can be used as the catalyst for hydrogenation of levulinic acid. The substrates for the catalyst can be chosen form alumina ($Al_2O_3$), magnesia (MgO) or zirconia ($ZrO_2$). Moreover, these substrates can be impure, thus the highest grade metal substrate is not required for the production of the hydrogenation catalyst.

If using a salt of any of the transition metal catalysts, these salts can be dissolved in ethanol or methanol. The substrate is also immersed in the solution, and then, removed and dried. This dried matrix, containing both the catalyst and substrate, is then placed in a kiln, and heated to 850–1000° C., for at least 30 minutes, followed by cooling before use in the hydrogenation reaction. If the catalysts become deactivated by the cooling process, they can be regenerated by reheating at 850–1000° C.

For each catalyst particle size, surface concentration of metal oxide species, ratio of catalyst used to reactor size, reactor volumes and temperatures, there will be a specific hydrogen pressure which will optimize the yield of MTHF without conversion of significant quantities of MTHF to 1,4-pentanediol. The other major constraint is temperature at the hydrogenation step. Excess temperatures can cause degradation of both starting products and lead to degradation of the desired end product. Generally it is preferred that the reactor temperature does not exceed 200° C.

EXAMPLE 15

As an example of the preparation of a catalyst for the hydrogenation reaction of levulinic acid to MTHF, 1–15 grams of Ni or Co acetate was dissolved in 40–50 ml of ethanol or methanol. 80–100 grams of roughly spherical alumina or zirconia particles of approximate diameter of ¼" diameter were placed in the liquid, removed, and dried for about 4 hours at 105° C. The particles were then placed in a kiln, which is heated to 850° C. (this heating step took 1.5 hours). The pellets were held at, or above, this temperature for 30 minutes, cooled and removed for use.

EXAMPLE 16

1 gram of copper acetate was placed in 40 ml of ethanol and 80 grams of $ZrO_2$ of roughly ¼" spheres was added. The $ZrO_2$/CuOAc was dried for 4 hours at 105° C. The mixture was then placed in a kiln and heated up to 850° C., where it was held at this temperature for 30 minutes.

The purpose of the heating step above is to convert the acetate salts to oxides which become bound to the substrate surface. The acetate salts form only $CO_2$ and water upon heating. However, although nitrate salts can be used for this process, these salts form toxic $NO_2$ instead upon decomposition, and thus, are less preferred.

What is claimed is:

1. A method of producing levulinic acid comprising:
   mixing biomass containing cellulose and hemicellulose with an acid to form an aqueous reaction solution which is 5–50% acid by weight while maintaining the temperature of the solution below about 60° C., thereby at least partially decrystallizing the biomass;
   heating said solution to about 80–200° C. for 1 to 30 hours, thereby hydrolyzing the cellulose and hemicellulose materials to sugars which are reacted following hydrolysis;
   separating the reaction products; and
   recovering levulinic acid.

2. The method of claim 1, wherein the acid is sulfuric acid.

3. The method of claim 1, wherein the concentration of said biomass is about 20–40% by weight in the reaction solution.

4. The method of claim 1, wherein the concentration of said biomass is about 30% by weight in the reaction solution.

5. The method of claim 1, wherein the concentration of cellulose is about 12–39% by weight in the reaction solution.

6. The method of claim 1, wherein the concentration of cellulose is about 21–30% by weight in the reaction solution.

7. The method of claim 1, wherein said biomass comprises rice straw materials.

8. The method of claim 1, wherein said biomass comprises woody plant materials.

9. The method of claim 1, wherein said biomass comprises paper materials.

10. The method of claim 1, wherein said biomass comprises cotton material.

11. The method of claim 1, wherein said biomass comprise cellulosic materials.

12. The method of claim 1, wherein said biomass comprises corn stalks.

13. The method of claim 1, wherein said biomass comprises bagasse.

14. The method of claim 1, wherein the step of heating said solution is conducted at 110–160° C.

15. The method of claim 1, wherein the concentration of the acid in the solution is about 10–30%.

16. The method of claim 1, wherein the step of heating the solution is conducted for 2 to 10 hours.

17. The method of claim 1, wherein the concentration of cellulose, the concentration of the acid and the temperature of the heating step are determined according to the equation:

$$A=0.4T+70-0.59(C-25.5);$$

wherein A is the percent sulfuric acid by weight in the reaction solution, T is the temperature in degrees Celsius, and C is the percent cellulose by weight in the reaction solution; and wherein the conditions used deviate from those obtained from the equation by not more than 5% by weight in the reaction solution for the value obtained for A, not more than 5% by weight in the reaction solution for the value obtained for C, and not more than 10° C. of the value obtained for T.

18. The method of claim 17, wherein the concentration of cellulose is 12–39% by weight in the reaction solution.

19. The method of claim 1, additionally comprising recovering a product selected from the group consisting of furfural, 5-HMF, succinic acid, maleic acid and fumaric acid.

20. The method of claim 1, wherein said product recovered is furfural.

21. The method of claim 1, wherein said products recovered is furfural and 5-HMF.

22. The method of claim 1, wherein the step of separating the products comprises chromatography.

23. The method of claim 1, wherein step of separating the products comprises chromatography using an ionic resin.

24. The method of claim 1, wherein step of separating the products comprises chromatography using an anionic resin.

25. The method of claim 1, wherein step of separating the products comprises chromatography using a multiple chromatographic columns.

26. The method of claim 1, additionally comprising:
hydrogenation of levulinic acid thus obtained in the presence of $H_2$ and a metal catalyst;
separating the reaction products; and
recovering methyltetrahydrofuran.

27. The method of claim 26, wherein ethanol is added during the hydrogenation step.

28. The method of claim 26, wherein the methyltetrahydrofuran is dried after the hydrogenation reaction, leaving a methyltetrahydrofuran product in a dry blend form.

29. The method of claim 26, wherein dry ethanol is added.

30. The method of claim 26, wherein the metal catalyst is Ni/Co catalyst.

31. The method of claim 1, additionally comprising dehydration of levulinic acid to yield a product comprising an angelica lactone.

32. The method of claim 1, additionally comprising filtering the reaction products prior to separation.

33. The method of claim 32, wherein the filter is washed with $H_2O$.

34. The method of claim 32, wherein both the first filtrate and second filtrate following the $H_2O$ washed are combined before separation.

35. The method of claim 1, wherein levulinic acid is concentrated after separation and recovery.

36. The method of claim 1, additionally comprising:
adding an alcohol to the levulinic acid;
refluxing the resulting alcoholic solution for 1–10 hours;
separating the mixture;
recovering levulinate ester.

37. The method of claim 36, wherein the reaction mixture is refluxed for 2–8 hours.

38. The method of claim 36, wherein the reaction mixture is refluxed for 3–6 hours.

* * * * *